United States Patent
Eisenhofer et al.

(10) Patent No.: US 10,219,710 B2
(45) Date of Patent: Mar. 5, 2019

(54) DEVICE FOR ADJUSTING AND DETERMINING THE BLOOD FLOW PLATEAU

(71) Applicant: TECHNISCHE UNIVERSITÄT DRESDEN, Dresden (DE)

(72) Inventors: Graeme Eisenhofer, Dresden (DE); Christina Pamporaki, Dresden (DE); Angelos Filippatos, Dresden (DE)

(73) Assignee: TECHNISCHE UNIVERSITÄT DRESDEN, Dresden (DE)

( * ) Notice: Subject to any disclaimer, the term of this patent is extended or adjusted under 35 U.S.C. 154(b) by 240 days.

(21) Appl. No.: 15/127,558

(22) PCT Filed: Jan. 30, 2015

(86) PCT No.: PCT/DE2015/100042
§ 371 (c)(1),
(2) Date: Sep. 20, 2016

(87) PCT Pub. No.: WO2015/144125
PCT Pub. Date: Oct. 1, 2015

(65) Prior Publication Data
US 2017/0127953 A1 May 11, 2017

(30) Foreign Application Priority Data
Mar. 26, 2014 (DE) .......................... 10 2014 104 167

(51) Int. Cl.
*A61B 5/02* (2006.01)
*A61B 5/026* (2006.01)
(Continued)

(52) U.S. Cl.
CPC .............. *A61B 5/0261* (2013.01); *A61B 5/01* (2013.01); *A61B 5/0295* (2013.01); *A61B 5/6806* (2013.01); *A61B 5/7282* (2013.01)

(58) Field of Classification Search
CPC ....... A61B 5/01; A61B 5/0261; A61B 5/0295; A61B 5/6806; A61B 5/7282
See application file for complete search history.

(56) References Cited

U.S. PATENT DOCUMENTS

| 2006/0195034 A1 | 8/2006 | Skrabal et al. |
| 2009/0287069 A1* | 11/2009 | Naghavi ................ A61B 5/417 600/309 |

(Continued)

FOREIGN PATENT DOCUMENTS

| EP | 1 929 980 B1 | 3/2012 |
| WO | 98/04182 A2 | 2/1998 |

(Continued)

OTHER PUBLICATIONS

International Search Report dated Apr. 30, 2015 in corresponding Application No. PCT/DE2015/100042; 3 pgs.

(Continued)

*Primary Examiner* — George Manuel
(74) *Attorney, Agent, or Firm* — Maier & Maier, PLLC (57) ABSTRACT

A device for adjusting and determining the blood flow plateau at a patient's limb, wherein the device includes an chamber the wall of which surrounds an inner space, and at least one opening for inserting at least a part of the limb into the inner space as well as at least one recess, that allows access to the part of the limb that is located inside the inner space, are formed in the chamber, and wherein the device includes at least one heating element that is in thermal contact with the inner space. In this context, it is provided that the device further includes an apparatus for determining the blood flow plateau at the part of the limb that is located inside the inner space.

15 Claims, 5 Drawing Sheets

(51) Int. Cl.
*A61B 5/01* (2006.01)
*A61B 5/0295* (2006.01)
*A61B 5/00* (2006.01)

(56) References Cited

U.S. PATENT DOCUMENTS

2010/0049007 A1    2/2010  Sterling et al.
2013/0184745 A1    7/2013  Leschinsky

FOREIGN PATENT DOCUMENTS

| WO | 2011/085268 A3 | 11/2011 |
| WO | 2013102051 A1 | 7/2013 |
| WO | 2013/143444 A1 | 10/2013 |

OTHER PUBLICATIONS

German Office Action dated Nov. 14, 2014, in connection with corresponding DE Application No. 10 2014 104 167.4 (2 pgs.).

* cited by examiner

DEVICE FOR ADJUSTING AND DETERMINING THE BLOOD FLOW PLATEAU

The invention relates to a device for adjusting and determining the blood flow plateau, particularly at a patient's limb.

Phaeochromocytoma are serious tumors. In general, these tumors produce specific hormones, the so-called monoamines, in a large amount. To diagnose the tumors there can be considered the concentration of metabolites of the produced monoamines in plasma, among others. Among these metabolites there are normetanephrine and metanephrine that together are referred to as metanephrines and when determining their concentration in the blood plasma as plasma metanephrines. However, the proportion of false-positive findings is high, especially if one would only consider the measurement of the normetanephrine in the plasma for diagnosis. However, to diagnose phaeochromocytoma normetanephrine is the more important one of both metabolites.

In the following, the term "plasma metanephrines" denotes both metabolites, whereas the terms "metanephrine" and "normetanephrine" each denote the individual metabolite.

It is known from the prior art that the arterial blood is more suitable for determining the concentration of the plasma metanephrines. However, in the clinical practice the measurement in the arterial blood is not easy to carry out. That's why it has not yet become relevant in practice. Usually, the measurement is performed on a patient's hand by the heating of which a vasodilation is to be achieved. This results in a reduced extraction of the arterial blood and a lower reaction of the sympathetic nervous system. In this way, not only the hormones are transmitted from the arterial to the venous blood without significant losses, but there is also eliminated the local normetanephrine release. For determining the normetanephrine concentration it is of significant importance to achieve the highest possible vasodilation level. If this vasodilation level is reached and then, the normetanephrine concentration is performed, so the false-positive measuring results for plasma metanephrine can be reduced.

In practice, so far blood was taken from the patients often at room temperature. However, there is a dependence between room temperature and the measured laboratory values that for example at low room temperatures results in an increase of false-positive findings. The warming up of the location of blood taking, i.e. generally the hand, causes a change in the local sympathetic norepinephrine release and a change in the local blood flow. Such a warming up is typically performed with an electric pad.

From EP 1 929 980 B1 there is known a device for adapting the blood circulation that can be a glove or a cuff. The device has a chamber into which the hand can be inserted. The wall of the chamber consists of two layers of a collapsible and pliant material. A fluid plenum is formed between the two layers through which a heat exchanging fluid should flow. Finally, there is provided a pump that is for generating a negative pressure in the chamber. The negative pressure is to ensure that the wall of the chamber directly fits to the hand surface.

WO 2011/085268 A9 is a further development of the device known from EP 1 929 980 B1. The device can additionally have sealed openings in the walls of the chamber that allow access to the hand surface and through which catheters can be inserted, for example. The device described in WO 2011/085268 A9 is to increase the blood flow and control the vasodilation of the patient's vascular structures.

WO 2013/143444 A1 discloses a method and a device for detecting vasodilation data. A heating element is provided for warming up the skin surface. Blood flow values from which vasodilation data are to be calculated are determined by means of a laser Doppler measuring instrument.

However, according to the prior art it is not possible to determine the suitable point of time for a blood taking beyond doubt. Thus, in practice the skin is warmed up for a prescribed period, generally 30 to 45 minutes. However, such a long-lasting warm up can cause pain in patients, in some cases even burns. On the other hand, the optimum point of time for the blood taking may have been already reached earlier, so that a warm up lasts unnecessarily long or a deterioration of the taking conditions already occurred again.

It is the object of the invention to eliminate the drawbacks according to the prior art. In particular, there is provided a device that allows a blood taking at a patient's limb at the point of time when the vasodilation has reached a greatest possible level. Here, the duration of the warm up and its maximum temperature should be as low as possible to minimize stresses of the patient.

This problem is solved by the features of claims 1, 12, and 15. Suitable developments of the inventions result from the features of the dependent claims.

According to the invention there is provided a device for adjusting and determining the blood flow plateau at a patient's limb, wherein the device comprises a chamber the wall of which surrounds an inner space. At least one opening for inserting at least a part of the limb into the inner space is provided in the chamber. Further, at least one recess is formed in the chamber that allows access to the part of the limb that is located inside the inner space. Additionally, the device possesses at least one heating element that is in thermal contact with the inner space. Moreover, the device comprises an apparatus for determining the blood flow plateau at the part of the limb that is located inside the inner space.

The invention allows the local warm up of a patient's limb whereby the maximum vasodilation is achieved. In this way, there is achieved an arterialization of the patient's blood, especially in the outer regions of the limb. At the same time, by means of the apparatus for determining the blood flow plateau the extent of vasodilation can be determined. If the highest possible vasodilation level is reached, so there can be taken a blood sample from the patient at the recess provided according to the invention that is suitable for determining the concentration of the plasma metanephrines. Such a blood sample allows a considerably more reliable diagnosis of a pheaochromocytoma. The number of false-positive measuring results is significantly reduced. Moreover, the blood sample can also be used to diagnose paragangliomas that indeed do not always produce hormones that can be measured in the blood sample.

The device according to the invention allows establishing the maximum vasodilation at a patient's limb in a relatively short time. This effect can be used in an advantageous manner in patients who are at an intensive care unit. In such patients a maximum vasodilation can be used to apply medicaments via the blood faster and/or in greater quantity.

Moreover, ascertaining the maximum vasodilation in a shorter time is of significant economic importance. In the clinical practice it can hardly be ensured so far that patients for a period of 30 min or even longer could be enabled to perform a local warm up with an electric pad in which the hand and the forearm have to be kept steady. Generally, for that there is lacking both the required space, especially in an outpatient treatment and the necessary time for the monitoring of the patient. Thus, a shortening of the period of the local warm up also decreases the costs of treatment.

The term "blood flow plateau" describes an area of largely constant flow rate of the peripheral blood in the limb after heat has started to act. If there is heat acting on a limb, first the flow rate of the peripheral blood for 2 to 3 minutes increases to a relative maximum and then, drops until a relative minimum is reached (phase 1 in FIG. 1). The relative minimum is above the flow rate before heat has started to act. After this relative minimum the flow rate of the blood again increases until it reaches a largely constant flow rate (phase 2 in FIG. 1), the so-called blood flow plateau. At the blood flow plateau the highest possible vasodilation level is present. The flow rate at the blood flow plateau is generally above the flow rate at the relative maximum. It may be provided for the purposes of the present invention that the blood flow plateau is considered to be reached if the measured flow rate of the blood for at least one minute, preferably for at least two minutes, is at a constant value with a tolerance of +/−10%, preferably +/−5%. The concrete value of the flow rate of the blood at the blood flow plateau both depends on the patient and the measuring method.

The device preferably comprises at least one measuring element for determining the temperature prevailing in the inner space. In the following, said measuring element is also referred to as measuring element for determining the inner space temperature. Further, there may be provided a control apparatus for controlling the heating element. Here, the control apparatus can comprise a data input for measured values of the measuring element for determining the temperature and for measured values of the apparatus for determining the blood flow plateau. The control apparatus can be connected to the heating element, the measuring element for determining the temperature, and the apparatus for determining the blood flow plateau via data lines, especially cables, for example. The inner space temperature corresponds to the surface temperature of the limb or the part thereof that is located inside the inner space of the device.

It may be provided that the heating element comprises at least one separate second measuring element for determining the temperature prevailing in the wall of the chamber directly at the heating element. In the following, said temperature is also referred to as temperature of the heating element or heating element temperature, the second measuring element as second measuring element for determining the heating element temperature. The temperature determined by means of the second measuring element for determining the heating element temperature can be used to control the heating element, namely as an alternative or in addition to the inner space temperature that is determined by means of the measuring element for determining the temperature in the inner space. For this purpose, the control apparatus can further comprise a data input for the measured values of the second measuring element for determining the temperature and can be connected thereto via a data line, especially a cable. At the same time, a power supply can be provided via the cable.

By the term "control of the heating element" there is understood the control of the heating power of the heating element.

The device can further comprise an evaluation unit that allows an evaluation of the measured values that are provided by the apparatus for determining the blood flow plateau. The evaluation unit can be part of the control apparatus. By means of the measured values provided by the apparatus for determining the blood flow plateau the evaluation unit examines whether the flow rate of the peripheral blood has reached the blood flow plateau. If this is the case, so then can be provided a signal unit that outputs a signal, for example an optical or acoustic signal or both. This signal informs the operator of the device that the conditions— namely the highest possible vasodilation level—for a blood taking now have been reached and that now the blood sample should be taken from the patient. The evaluation unit may be part of the control apparatus.

The heating element is for continuously delivering heat to the limb that is located inside the inner space. Preferably, the heating element is an electrical heating element that converts electrical energy into thermal energy. The heating element may be an electric pad. By the control apparatus there may be given a maximum temperature that is to be reached in the inner space. The maximum temperature may be for example at 44° C. With the start of warming up the temperature in the inner space is preferably uniformly increased. At the same time the blood flow is measured. As soon as the blood flow plateau is reached the warm up can be terminated or reduced. According to the findings of the inventors the blood flow plateau, compared to the prior art, is reached in a shorter time and at lower temperatures, i.e. temperatures below 44° C. According to the prior art a warm up was provided for at least 30 min, often for 45 min. Thus, by means of the device according to the invention at the same time there is reduced the stress associated with the preparation of the blood taking. Pain and burns at the limb are prevented. The device according to the invention can comprise a plurality of heating elements. Each of the heating elements can comprise one or more thermocouples. Such a thermocouple may be a wire that warms up if electric power is supplied to it. The wire may be a metallic wire or a carbon fiber wire. Such wires generate infrared heat with which a warm up of the inner space and thus, the surface of the limb can be achieved in a fast, safe, and efficient manner. The operating voltage for the supply of the heating element with electric energy is preferably 24 V what is considered as "non-hazardous low voltage".

The control apparatus that can comprise the evaluation unit and the signal unit both processes the measured values for the inner space temperature, i.e. also that for the blood flow, and controls the heating element such that a uniform rise in temperature of the inner space temperature to the maximum, for example at most 45° C., is achieved.

Further, the control apparatus can have a power supply to supply apparatuses and elements of the device, as far as required, with electric current.

It may be provided that the heating element, the apparatus for determining the blood flow plateau and the measuring elements for determining the inner space temperature and/or the heating element temperature are integrated into the wall of the chamber. In one embodiment of the invention it is provided that the wall of the chamber is formed multi-layered with a first inner layer facing the inner space and a second outer layer, wherein the heating element, the apparatus for determining the blood flow plateau, and the measuring element for determining the inner space temperature and, if present, the second measuring element for determining the heating element temperature are arranged between the first layer and the second layer.

Preferably, the chamber is formed of a flexible material. This has the advantage that the device can be pulled on the limb of the patient, for example his/her hand and forearm, by inserting the limb into the opening formed in the chamber.

Thus, there is not required a pump or another apparatus for adjusting a negative pressure in the inner space of the chamber. Because no negative pressure has to be generated it is also not required to seal the opening through which the limb is inserted into the inner space or the recesses formed in the wall of the chamber against the environment in a pressure-tight manner. However, there may be provided a fastening means for fixing the device at the patient's limb, for example a belt or a strap, wherein actually a plurality of such fastening means can be used. The first layer and the second layer both should consist of a flexible material. Preferably, they consist of the same material.

The wall of the chamber of the device according to the invention can be single or multi-layered. The layers each should consist of a flexible material. The flexible material may be for example a plastic or a textile material. The plastic may be selected from the group comprising polyurethanes, polypropylenes, polystyrene, polyethylene, for example high-density polyethylene (HDPE) or low-density polyethylene (LDPE), polyvinyl chloride and mixtures thereof. Preferably, the textile material is a non-woven, particularly preferred a polyester-based non-woven.

The flexible material may be an elastic material. The elastic material allows that the chamber can be stretched for pulling onto the limb and then contracts such that it tightly fits to the surface of the part of the limb that is located inside the inner space. However, there can also be used other materials that are not elastic or only to a low extent, for example textile materials such as non-wovens. In the following, such materials are referred to as "non-elastic materials", even if they may have a certain elasticity. It is true that non-elastic materials can only be stretched to a low extent and also only contract to the same extent. Non-elastic materials have the advantage that they do not apply pressure to the surface of the limb or the part thereof that are located inside the inner space of the device according to the invention. Such a pressure could affect the quality of the measurement or the composition of the blood what is undesired. For fixation of the device according to the invention at the patient's limb the fastening means are sufficient. Non-elastic materials are preferred. However, in case of a multi-layer wall it may be provided that a part of the layers consists of non-elastic materials and the remaining part of elastic materials, wherein the wall in total is not elastic or—compared with elastic materials—only to a low extent.

If the wall of the chamber has a first inner layer and a second outer layer, so the first layer should consist of an allergy-tested flexible material, i.e. a material that does not cause allergic reactions on the skin of the limb that is located inside the inner space of the chamber. The second layer particularly should consist of a waterproof flexible material. Preferably, the first and the second layer consist of a textile material, for example a non-woven.

In one embodiment of the invention the heating element, the apparatus for determining the blood flow plateau, and the measuring element for determining the temperature inside the inner space are arranged between the first layer and the second layer. Here, it may be provided that the apparatus for determining the blood flow plateau and the measuring element for determining the temperature inside the inner space adjoin the first layer. The measuring element for determining the temperature inside the inner space should be arranged thermally insulated to the heating element by means of an insulation material. It may be provided that also the apparatus for determining the blood flow plateau is arranged thermally insulated to the heating element by means of an insulation material. The sensor of the measuring element for determining the temperature inside the inner space should be in contact with the surface of the limb when this is inserted into the inner space of the chamber. For that, there may be formed an opening in the first layer that surrounds the sensor. Preferably, the apparatus for determining the blood flow plateau and the measuring element for determining the temperature inside the inner space in common are embedded in a third layer of the chamber that is adjacent to the first layer despite of the region of the skin contact of the sensors. Also the third layer can be formed of a non-woven, for example the same non-woven as the first and/or second layer. The heating element and, if present, the second measuring element for determining the temperature of the heating element may be formed as a fourth layer that is adjacent to the third layer.

Preferably, the measuring element for determining the temperature inside the inner space is a temperature sensor. The device can comprise several measuring elements for determining the inner space temperature, especially several temperature sensors. Preferably, also the second measuring element for determining the temperature of the heating element is a temperature sensor. The device can comprise several second measuring elements for determining the heating element temperature, especially several temperature sensors.

The fourth layer may be followed by a fifth layer consisting of an insulation material that thermally insulates the second layer from the fourth layer. The insulation material may be a plastic. Here, it may be the same plastic the insulation material of the third layer consists of.

The insulation material may be aluminum or silicone, wherein for the device there is suitably selected only one type of insulation material. In addition to the thermal insulation the insulation material also serves to shield the measuring element for determining the inner space temperature and the apparatus for determining the blood flow.

Then, the fifth layer is followed by the second, outer layer. The layers the wall of the chamber consists of preferably are inseparably connected to each other, for example they may be welded or glued.

The apparatus for determining the blood flow plateau may be any apparatus that according to the prior art is used for determining the blood flow plateau. Preferably, the apparatus for determining the blood flow plateau is a laser Doppler anemometer or a strain gauge plethysmograph with a laser Doppler anemometer being particularly preferred. In the medical practice laser Doppler anemometers are sometimes also referred to as laser Doppler haemodromometers or laser Doppler flowmeters, the associated measuring method as laser Doppler flowmetry. Strain gauge plethysmographs, sometimes also referred to as strain gauge plethysmography devices, use the occlusion plethysmography as measuring method for determining the blood flow. By means of the apparatus for determining the blood flow plateau the peripheral blood flow, i.e. the flow rate of the blood in peripheral blood vessels, is suitably continuously measured. If the laser Doppler flowmetry is employed, so the flow rate of the blood is measured in so-called "perfusion units", abbreviated PU, with 1 PU corresponding to 10 mV. The unit of the flow rate for the strain gauge plethysmography is the blood flow BF, where 1 BF corresponds to 1 ml/100 ml/min According to the invention the device is provided for adjusting and determining the blood flow plateau at a patient's limb. The limb especially may be a hand, a forearm, a hand and the adjoining complete forearm or a part of the forearm, a foot, a lower leg, a foot and the complete adjoining lower leg or a part of the lower leg. In a preferred embodiment the device is provided for adjusting and determining the blood flow plateau at a hand and the adjoining forearm or a part of the forearm. In this case, the chamber of the device may be in the form of a glove the inner space of which is adapted to accommodate a patient's hand and his/her forearm or a part thereof.

If the device for adjusting and determining the blood flow plateau according to the invention is in the form of a glove into which the hand and the forearm of the patient are to be inserted, so the sensor of the measuring element for determining the inner space temperature should be located in a region that at the forearm adjoins the wrist.

Preferably, there are formed two recesses in the chamber that allow access to the part of the limb that is located inside its inner space. The recess may be adapted such that a catheter, for example a venous catheter, a tube, a cannula, for example a venous cannula, or a measuring apparatus, for example a thermostat probe, each alone or together can be passed through the recess to the limb that is located inside the inner space of the chamber. Preferably, the recess is adapted such that a cannula, in particular a venous cannula, together with a thermostat probe can be passed to the limb. Suitably, there are provided covers for the recesses with which the recesses can be sealed in a heat-tight manner. In this way, the heat exchange between the inner space and the environment via the recesses should be minimized or completely prevented, what provides for a homogeneous temperature distribution within the inner space.

If the chamber is in the form of a glove into the inner space of which a patient's hand and forearm can partially or completely be inserted, so it may be provided that the inner space has a first part for accommodating the hand and a second part for accommodating the forearm or a part thereof. Here, a first recess can be formed in a section of the wall that surrounds the first part of the inner space. A second recess can be formed in a section of the wall that surrounds the second part of the inner space. Preferably, here the first recess is formed in a region of the wall that constitutes the palm of the glove, whereas the second recess is formed in a region that adjoins the opening for inserting at least a part of the limb. Here, both recesses should lie on a straight line that is in parallel to the longitudinal axis of the glove. If the hand and the forearm are inserted into the glove through the opening, so thus, the first recess is located at the distal end of the glove, while the second recess is located at the proximal end that adjoins the patient's elbow.

According to the invention there is further provided a method for adjusting and determining the blood flow plateau at a patient's limb by means of a device according to the invention comprising the steps of (a) inserting a limb into the inner space of the chamber, so that at least a part of the limb is located inside the inner space of the chamber;

(b) supplying thermal energy to the part of the limb by means of the heating element and continuously determining the temperature inside the inner space and the blood flow at the part of the limb; and (c) outputting a signal if the blood flow has reached the blood flow plateau.

The output of the signal informs the user of the device according to the invention that there are optimum conditions for taking a blood sample from the patient. This sample is particularly suitable for determining the concentration of plasma metanephrines when there should be found or excluded a phaeochromocytoma with the help of the measured values.

Preferably, it may be provided that the point of time of reaching the blood flow plateau starting from the beginning of the warm up in step (b) and the temperature inside the inner space at which the blood flow reaches the blood flow plateau are detected.

It may further be provided that the supply of thermal energy is reduced or stopped by means of the heating element as soon as the blood flow plateau is reached.

Moreover, according to the invention there is provided the use of a device for adjusting and determining the blood flow plateau at a patient's limb according to the invention. Here, the device according to the invention and the method according to the invention are not limited to the adjustment of conditions that are suitable for taking a blood sample that is to be used for the diagnosis of phaeochromocytoma or paraganglioma. There may also be adjusted conditions, especially temperature and blood flow, that are of advantage for other purposes.

The invention among others is based on the following considerations. Perfusion of the skin can be measured by means of the laser Doppler flowmetry. In this way, the peripheral blood flow can be determined. The recent studies show that the local skin warming of the forearm causes an increase in skin blood flow in two phases. A first rapid blood flow increase is observed within 2 to 3 minutes after the start of the warm up. This is followed by a short blood flow decline that after 20 to 30 minutes stays on a certain plateau, the blood flow plateau (see FIG. 1). A key factor here is the finding that this plateau depends on vascular factors. For example, patients with peripheral micro-vascular dysfunctions that inter alia may occur in case of cardiovascular diseases showed a reduced vasodilation. It should be noted that patients who were treated with statins showed a deeper blood flow plateau. In case of a long-lasting warm up there is sometimes observed a phenomenon referred to as "die away". This phenomenon in which the blood flow slowly goes back to its starting point normally occurs 45 minutes after the start of the warm up. That's why the warm up protocols have a duration of 30 to 45 minutes. However, so far there are no available results of research for patients with noticeable peripheral dysfunctions or restricted vasodilation capacity. In these patients there is often observed a deeper blood flow plateau that possible occurs before the expected time, in general 45 minutes. In this context, a premature "die away" phenomenon could appear what impairs the expressiveness of a blood sample that is taken after the start of the "die away".

Thus, the inventors have found that it is not sufficient only to use a conventional heater, since in this way it cannot be determined whether and when the desired vasodilation occurs. Moreover, the vasodilation level cannot be established and also the exact time of the blood flow plateau remains unknown. Considering the above-mentioned facts the simultaneous warm up of the limb and the blood flow evaluation are critical to diagnose or exclude a phaeochromocytoma or paraganglioma. Experiments the inventors carried out with conventional heaters using laser Doppler flowmetry or gauge plethysmographs confirmed that the arterialization in general can be achieved with the local warm up of the forearm, but also showed that there are significant restrictions that required the development of a new instrument, namely the device according to the invention.

Figure 1:
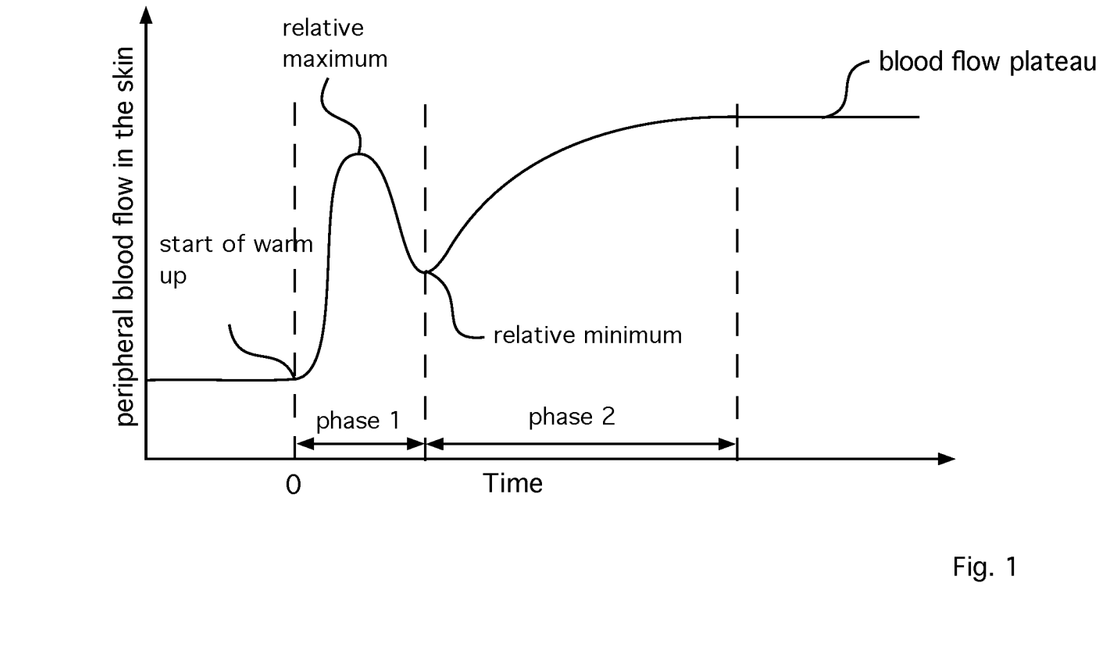
FIG. 1 shows a chart schematically showing the change in blood flow depending on the duration of warm up.

There are different warm up protocols for the local application of heat to the surface of a limb in which normally a temperature of 42 to 44° C. is recommended. At this temperature, as shown in FIG. 1, there is caused a vasodilation in two phases, i.e. a first phase comprising the increase in flow rate with the start of the warm up to up to the relative maximum and the drop of the flow rate up to the relative minimum, and a second phase comprising the increase in flow rate from the relative minimum until the blood flow plateau is reached.

The electric pads employed according to the prior art for the local warm up of the skin surface with temperatures of 42 to 44° C. could result in a warm up of the skin surface to temperatures above the temperature of the electric pad. The temperature of the skin surface was not measured. Even though a local warm up to a temperature of 42 to 44° C. as well as a long-lasting warm up to said temperatures is well tolerated by most of the test persons in patients with abnormal micro-vascular function it sometimes results in complaints such as pain or burns, particularly when the temperature on the skin surface was still above the temperature of the electric pad. Therefore, such patients so far were excluded from the arterialization by means of warm up. The device according to the invention can also be used in such patients, because the time for the warm up is significantly shorter, because in such patients the highest possible vasodilation level appears earlier and at lower temperatures.

When using the device according to the invention it is established when the blood flow plateau is reached. For that, the device according to the invention can output the exact time and the temperature of the inner space. Thus, a warm up of the limb of 30 min or even longer is avoided. If the blood flow plateau is reached at an inner space temperature of less than 44° C., so the device according to the invention warms up the limb only to this temperature level, wherein subsequently it holds the temperature on this temperature level.

The inventors have found that certainly even in combination with the laser Doppler flowmetry conventional heaters in many cases achieve the arterialization and can measure it. But such a combination is not capable to simultaneously warm up and mathematically determine the blood flow plateau, since there is lacking a resulting controlled temperature adjustment with respect to the limb.

On the basis of these findings the device according to the invention was developed that during the local warm up of a limb, especially the forearm, in each patient determines the exact time and temperature of the blood flow plateau. By means of the control apparatus of the device according to the invention the temperature of the inner space can stably be adjusted to a temperature of less than or equal to 44° C. in order to avoid an unnecessarily higher warm up of the limb and thus, possible side effects. The device according to the invention can inform the user by means of a signal, for example with a characteristic sound, as soon as the blood flow level has been reached and thus, there prevail conditions that are suitable to take a blood sample. In this way, an unnecessarily long-lasting warm up is avoided and thus, the risk of the "die away" phenomenon is excluded.

By the ideally controlled blood flow temperature measurements the side effects of the prolonged warm up are reduced.

By means of the invention the diagnostic efficiency and diagnostic reliability can be enhanced, because the blood sample can be taken at a point of time at which optimum conditions are present, so that it can reliably be deduced the presence or absence of a phaeochromocytoma from the concentration of the plasma metanephrines in this blood sample. The analysis of the blood sample is facilitated, because both the temperature upon the sampling and the blood flow are known and are adjusted to ideal values.

The control apparatus of the device according to the invention can ensure that the arterialization of the blood and thus, the maximum vasodilation can be realized at an optimized temperature regime. The sampling that so far could be performed after 30 to 45 minutes takes place within a short time now, because the blood flow plateau is reached more quickly. In this way, complaints such as pain and burns are prevented. Moreover, there is determined the temperature prevailing inside the inner space of the chamber when the blood flow plateau is reached.

In the following, the invention is explained in greater detail by way of examples that are not intended to limit the invention with respect to the drawings. Here.

Figure 2:
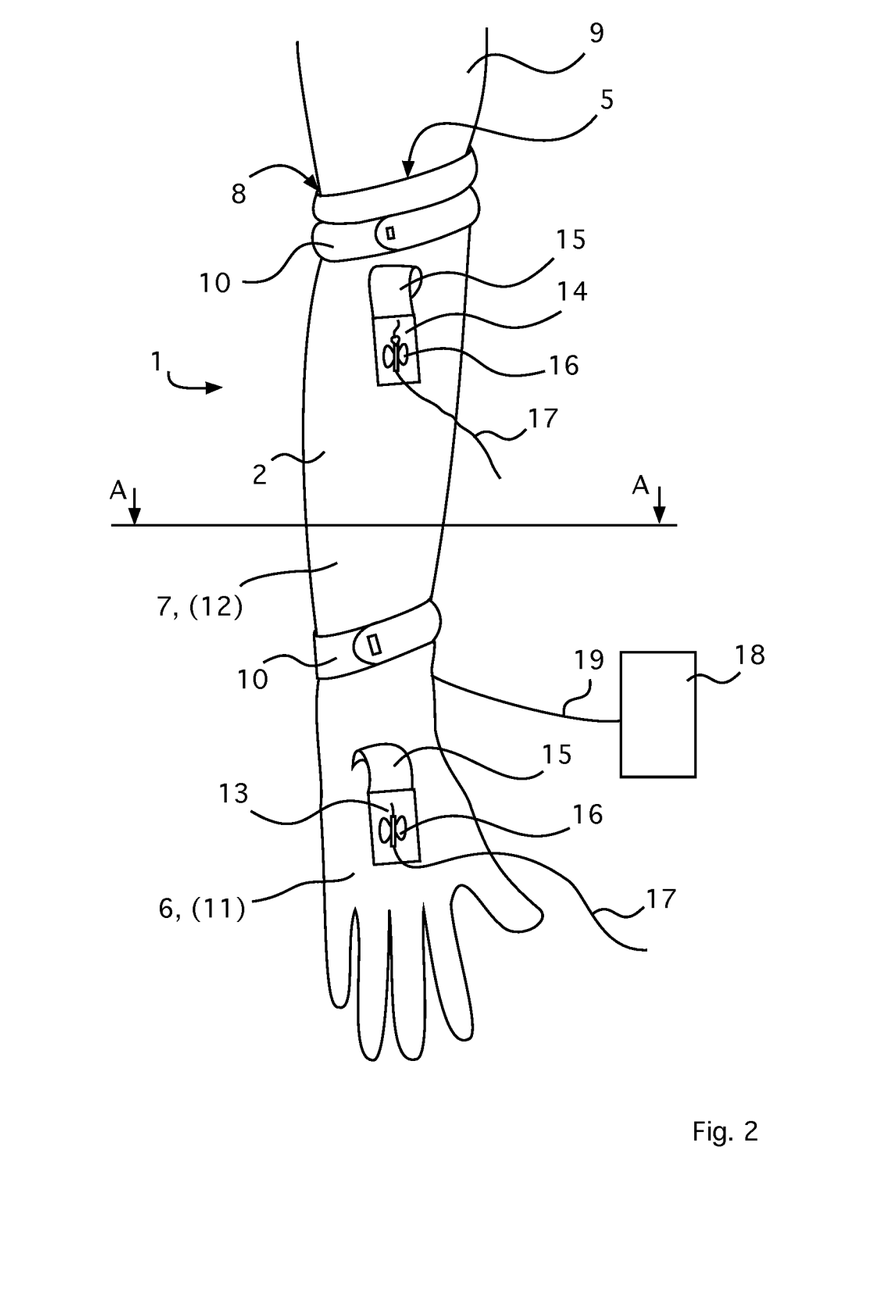
FIG. 2 shows a view of an embodiment of a device for adjusting and determining the blood flow plateau at a patient's hand and forearm according to the invention.
Figure 3:
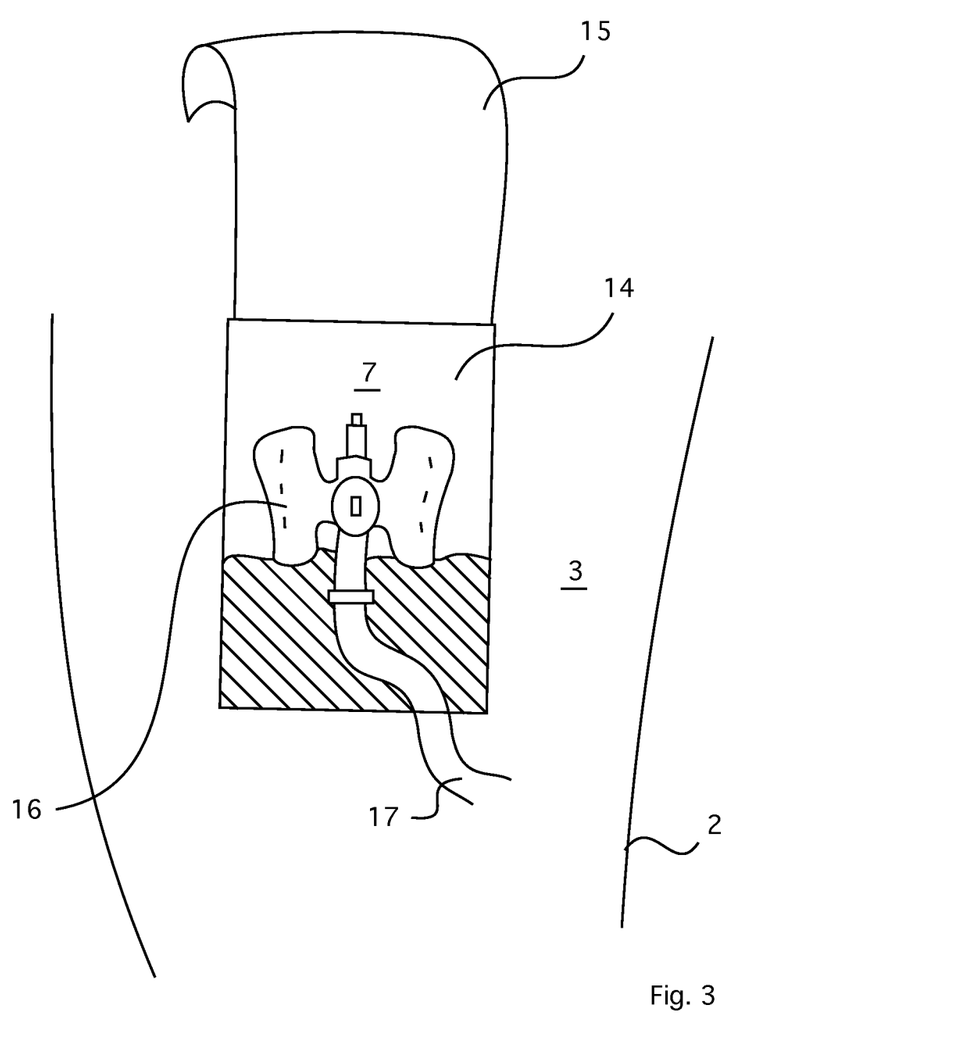
FIG. 3 shows a detailed view of the embodiment shown in FIG. 2.
Figure 4:
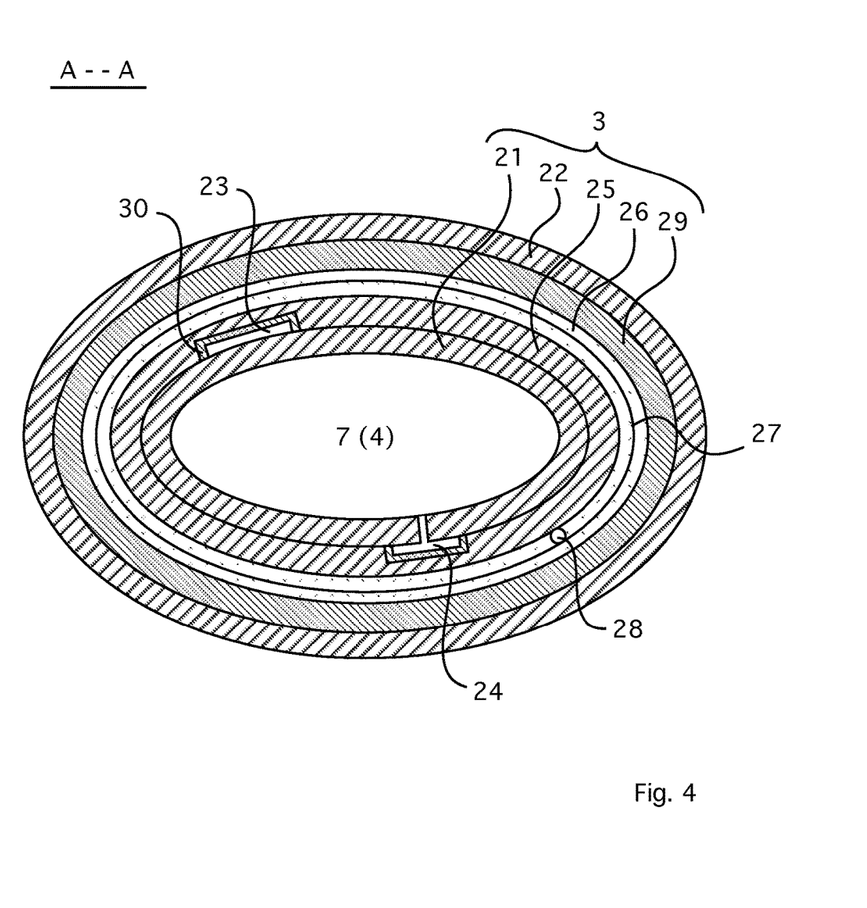
FIG. 4 shows a schematic sectional view along line A-A in FIG. 3.

The embodiment of a device 1 according to the invention shown in FIGS. 2 to 4 comprises a chamber 2 in the form of a glove. Therefore, the chamber 2 can also be referred to as a glove. The wall 3 of the chamber 2 surrounds an inner space 4. An opening 5 is formed in the wall through which the hand 6 and the forearm 7 of a patient can be inserted into the inner space 3 up to his/her elbow. In FIGS. 2 to 4 the hand 6 and forearm 7 of the patient are located inside the inner space 4 of the chamber 2. Here, the wall 3 extends to the elbow 8 of the patient, so that his/her upper arm 9 is exposed. Here, the glove-shaped chamber 2 is fixed to the forearm 7 of the patient by means of belts 10. Here, a first belt 10 is attached to the elbow 8 of the patient, a second belt 10 is attached above the wrist of the hand 6.

The inner space 4 has a first part 11 and a second part 12. In the first part 11 of the inner space 4 there is the hand 6, in the second part 12 of the inner space 4 the forearm 7. Recesses 13, 14 are formed in the wall 3 of the glove-shaped chamber 2 that allow access to the hand 6 and the forearm 7. It is apparent in FIG. 2 that the first recess 13 is formed in a region of the wall 3 that surrounds the first part 11 of the inner space 4. Here, the first recess 13 is arranged such that it is located in the region of the palm of the glove-shaped chamber 2. The palm of the glove-shaped chamber 2 is the part of the wall 3 that adjoins the palm of the hand 6. The second recess 14 is formed in a region of the wall 3 that is adjacent to the opening 5. Both recesses 13, 14 lie on a straight line that extends in parallel to the longitudinal axis of the glove-shaped chamber. Thus, the first recess 13 is located at the distal end of the glove-shaped chamber 2, whereas the second recess 14 is located at the proximal end of the glove-shaped chamber 2 that adjoins the elbow 8 of the patient. At the edge of recesses 13, 14 each there are covers 15 that are intended to seal the recesses 13, 14 in a heat-tight manner. The covers can be the part of the wall 3 that had to be separated from the remaining wall 3 for creating the recesses 13, 14.

The recesses 13, 14 allow access to the limb, i.e. the hand 6 and the forearm 7. For example, a venous cannula 16 can be passed to the limb that is located inside the inner space 4 of the chamber 2 via recesses 13, 14. In FIG. 3, the second recess 14 is shown that allows access to the forearm 7. A venous cannula 16 is passed through the second recess 14. Each of the venous cannulas 16 can be connected to a fluid passing means, for example a tube 17.

In FIG. 2, a venous cannula 16 is illustrated in both recesses 13, 14. However, in general only one venous cannula 16 is required to take a blood sample. Suitably, the venous cannula 16 is inserted into one of the recesses 14 before it is started to supply heat via the heating element 27 in order to be able to take the blood sample directly after the output of the signal. In most of the patients the second recess 14 should be used to attach a venous cannula 16 for the blood sample. However, in some cases it may be suitable to use the first recess 13 for that. After the venous cannula 16 has been inserted into one of the recesses 13, 14 both recesses should be closed by means of covers 15. Only then supply of heat via the heating element 27 should be started.

As shown in FIG. 4, the wall 3 of the chamber 2 has a first inner layer 21 and a second outer layer 22. The first layer 21 that separates the inner space 4 and adjoins the hand 6 and the forearm 7 that are located inside the inner space 4 consists of an allergy-tested flexible material. The second layer 22 consists of a watertight flexible material. It forms the outside of the wall 3. Preferably, the first layer 21 and the second layer 22 consist of a non-woven fabric, particularly preferred of the same non-woven fabric. The non-woven fabric may be a polyester-based non-woven fabric.

A third layer 25 of a non-woven fabric is arranged between the first layer 21 and the second layer 22. The third layer can consist of the same non-woven fabric as the first layer 21 and/or the second layer 22. The laser Doppler haemodromometer 23 (or another apparatus for determining the blood flow, for example a strain gauge plethysmograph) and a first temperature sensor 24 are embedded into the third layer 25. The first temperature sensor 24 is in contact with the inner space 4, so that it can detect the inner space temperature and thus, the surface temperature of the forearm. Here, the laser Doppler haemodromometer 23 is arranged such that it can emit light through the first layer 21 into the forearm 7 and receive the light remitted there. Layers of an insulation material are provided within the third layer that thermally insulate the laser Doppler haemodromometer 23 and the first temperature sensor 24 for the determination of the inner space temperature from an electric heating element 27 that is arranged in a fourth layer 26 together with a second temperature sensor 28 for determining the temperature of the heating element 27. The insulation material 30 may be aluminum or silicone. The fourth layer 26 is adjacent to the third layer 25. Finally, a fifth layer 29 of an insulation material, for example aluminum or silicone is formed between the fourth layer 26 and the second outer layer 22 and insulates the second layer 22 from the heating element 27. The heating element comprises a plurality of thermocouples, for example wires of metal or carbon.

For receiving the measured values from the first temperature sensor 24, the second temperature sensor 28, and the laser Doppler haemodromometer 23 as well as for controlling the heating element 27 a control apparatus 28 is provided. The control apparatus is connected to the first temperature sensor 24, the second temperature sensor 28, the laser Doppler haemodromometer 23, the heating element 27 as well as the thermostat sensors at the recesses 13, 14 via an electric cable 19. The control apparatus 18 comprises the evaluation unit and the signal unit (both not shown).

Figure 5:
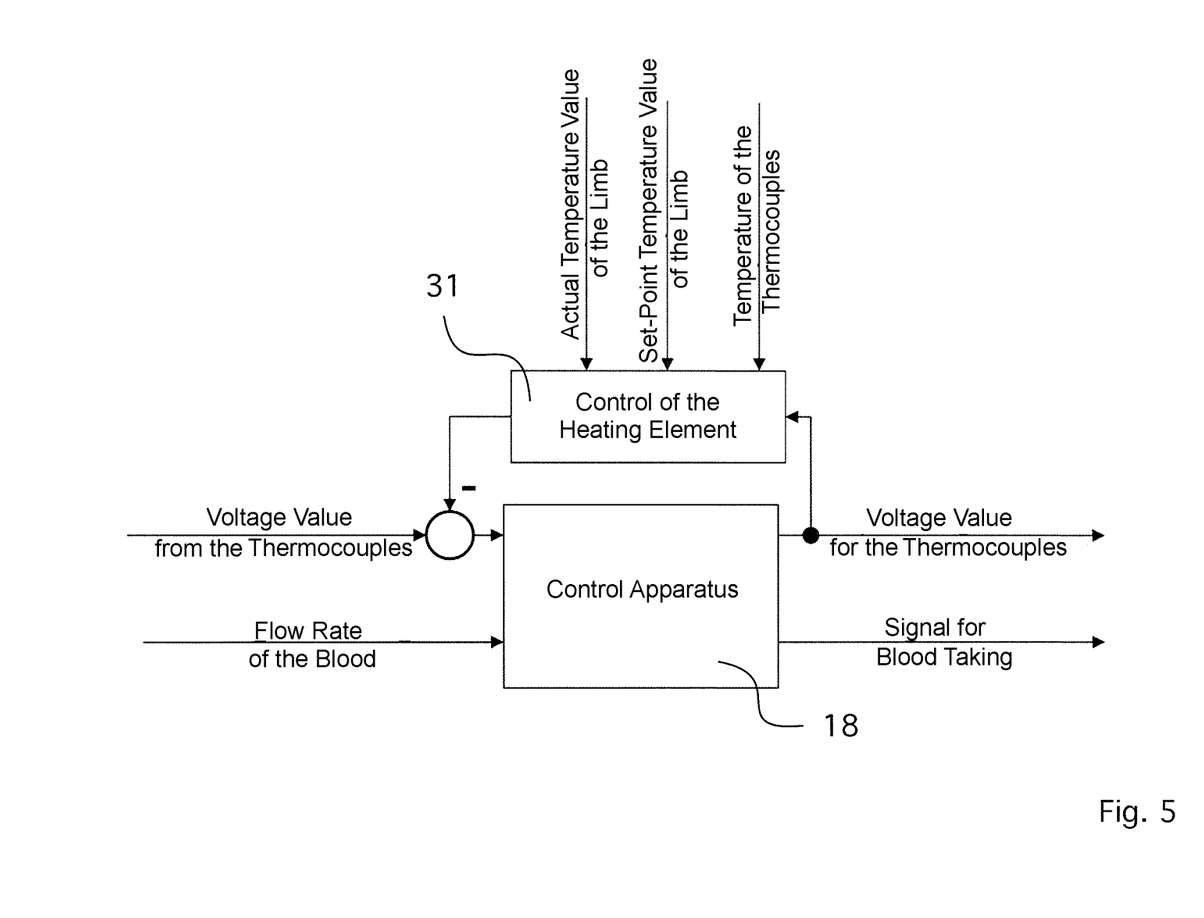
FIG. 5 shows an exemplary signal flow chart for controlling the heating element of the embodiment of the device according to the invention shown in FIGS. 1 to 4.

The signal flow chart shown in FIG. 5 is an example of the control of the heating element of a device according to the invention. Input values for controlling the heating element are the actual temperature of the limb or the part thereof that is located inside the inner space 4, the set-point temperature of the limb or of the part thereof that is located inside the inner space 4, and the temperature of the thermocouples of the heating element 27. The actual temperature of the limb or the part thereof that is located inside the inner space 4 is determined by means of the first temperature sensor 24. The set-point temperature of the limb or the part thereof that is located inside the inner space 4 is given by the user of the device according to the invention. The temperature of the thermocouple of the heating element 27 is determined by means of the second temperature sensor 28. The values for these three input values that are detected by the controller 31 at the summing point are combined with the voltage value of the heating element as a fourth input value. The output value is the voltage value of the heating element. Also, the voltage value is detected and led back to the controller 31 at the branch point. The control should take place automatically.

A further input value is the flow rate of the blood that however has not been taken up in the control of the heating element 27. The flow rate of the blood is detected to be able to output a signal when the blood flow plateau is reached.

LIST OF REFERENCE NUMBERS

1 device
2 chamber
3 wall
4 inner space
5 opening
6 hand
7 forearm
8 elbow
9 upper arm
10 belt
11 first part of the inner space
12 second part of the inner space
13 first recess
14 second recess
15 cover
16 venous cannula
17 tube
18 control apparatus
19 cable
21 first inner layer
22 second outer layer
23 laser Doppler haemodromometer
24 first temperature sensor
25 third layer
26 fourth layer
27 heating element
28 second temperature sensor
29 fifth layer
30 insulation material
31 controller

The invention claimed is:

1. A device for adjusting and determining the blood flow plateau at a patient's limb, wherein the device comprises:
a chamber the wall of which surrounds an inner space, and at least one opening for inserting at least a part of the limb into the inner space and at least one recess, that allows access to the part of the limb that is located inside the inner space, are formed in the chamber, wherein the at least one recess is disposed through the wall of the chamber, and
wherein the device comprises at least one heating element that is in thermal contact with the inner space, wherein the device further comprises an apparatus for determining the blood flow plateau at the part of the limb that is located inside the inner space.

2. The device according to claim 1, wherein it comprises at least one measuring element for determining the temperature inside the inner space.

3. The device according to claim 2, wherein it comprises a control apparatus for controlling the heating element, wherein the control apparatus comprises a data input for measured values from the measuring element for determining the temperature inside the inner space and for measured values from the apparatus for determining the blood flow plateau.

4. The device according to claim 1, wherein it comprises an evaluation unit that allows an evaluation of the measured values of the apparatus for determining the blood flow plateau, and a signal unit that allows the output of a signal when the blood flow plateau is reached.

5. The device according to claim 1, wherein the heating element, the apparatus for determining the blood flow plateau, and the measuring element for determining the temperature inside the inner space are integrated in the wall of the chamber.

6. The device according to claim 1, wherein the wall of the chamber is formed multi-layered with a first inner layer facing the inner space and a second outer layer, wherein the heating element, the apparatus for determining the blood flow plateau, and the measuring element for determining the temperature inside the inner space are arranged between the first layer and the second layer.

7. The device according to claim 1, wherein the apparatus for determining the blood flow plateau is a laser Doppler anemometer or a strain gauge plethysmograph.

8. The device according to claim 1, wherein it comprises at least one fastening means for fixing the device on the patient's limb.

9. The device according to claim 1, wherein the chamber is a glove the inner space of which is adapted such that it can accommodate the hand of a patient and his/her forearm or a part thereof.

10. The device according to claim 9, wherein the inner space of the glove comprises a first part for accommodating the hand and a second part for accommodating the forearm or a part thereof, wherein a first recess is formed in a section of the wall that surrounds the first part of the inner space, and a second recess is formed in a section of the wall that surrounds the second part of the inner space, wherein the first recess is formed in a region that constitutes the palm of the glove and the second recess is formed in a region that adjoins the opening for inserting at least a part of the limb.

11. The device according to claim 1, wherein a thermostat probe is arranged at the recess.

12. A method for adjusting and determining the blood flow plateau at a patient's limb by means of a device according to claim 1 comprising the steps of
(a) inserting a limb into the inner space of the chamber, so that at least a part of the limb is located inside the inner space of the chamber;
(b) supplying thermal energy to the part of the limb by means of the heating element and continuously determining the temperature inside the inner space and the blood flow at the part of the limb; and
(c) outputting a signal when the blood flow has reached the blood flow plateau.

13. The method according to claim 12, wherein the point of time when the blood flow plateau is reached and the temperature inside the inner space at which the blood flow reaches the blood flow plateau are detected.

14. The method according to claim 12, wherein the supply of thermal energy in step (b) is reduced or stopped as soon as the blood flow plateau is reached.

15. Use of a device according to claim 1, for adjusting and determining the blood flow plateau at a patient's limb.

* * * * *